(12) United States Patent
Han et al.

(10) Patent No.: US 10,466,785 B2
(45) Date of Patent: Nov. 5, 2019

(54) DISPLAY SYSTEM FOR PHYSIOLOGICAL INFORMATION AND DIAGNOSTIC METHOD

(71) Applicant: BOE TECHNOLOGY GROUP CO., LTD., Beijing (CN)

(72) Inventors: Yang Han, Beijing (CN); Tianyue Zhao, Beijing (CN); Weiqiang Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 14/441,409

(22) PCT Filed: Nov. 20, 2014

(86) PCT No.: PCT/CN2014/091787
§ 371 (c)(1),
(2) Date: May 7, 2015

(87) PCT Pub. No.: WO2015/154471
PCT Pub. Date: Oct. 15, 2015

(65) Prior Publication Data
US 2016/0048206 A1    Feb. 18, 2016

(30) Foreign Application Priority Data

Apr. 11, 2014  (CN) .......................... 2014 1 0145595

(51) Int. Cl.
*G06F 3/01*         (2006.01)
*A61B 5/00*         (2006.01)
(Continued)

(52) U.S. Cl.
CPC .............. *G06F 3/015* (2013.01); *A61B 5/742* (2013.01); *A61B 5/002* (2013.01); *A61B 5/7264* (2013.01); *A61B 7/04* (2013.01); *G06F 19/3418* (2013.01)

(58) Field of Classification Search
None
See application file for complete search history.

(56) References Cited

U.S. PATENT DOCUMENTS

2006/0111639 A1 * 5/2006 Su ........................ A61B 5/0002
                                                          600/493
2007/0123786 A1   5/2007 Grandjean et al.
(Continued)

FOREIGN PATENT DOCUMENTS

CN       1965752 A     5/2007
CN     101032427 A     9/2007
(Continued)

OTHER PUBLICATIONS

Written Opinion of the International Searching Authority dated Mar. 4, 2015 corresponding to International application No. PCT/CN2014/091787.
(Continued)

*Primary Examiner* — David D Davis
(74) *Attorney, Agent, or Firm* — Nath, Goldberg & Meyer; Joshua B. Goldberg; Daniel Bissing

(57) ABSTRACT

The present invention provides a display system and a diagnostic method. The display system includes an information preprocessing module, a display panel and a control circuit electrically connected to the display panel. The information preprocessing module is used for starting the control circuit and the display panel. The control circuit is used for controlling the display panel to display an image. The information preprocessing module includes a sensor used for collecting physiological information of human body (Continued)

and a preprocessing circuit used for preprocessing the physiological information of human body collected by the sensor and transmitting the preprocessed physiological information of human body to the control circuit. The control circuit is used for receiving and diagnosing the preprocessed physiological information of human body to obtain a diagnosis result. The display panel is used for displaying the diagnosis result.

14 Claims, 3 Drawing Sheets

(51) Int. Cl.
    *A61B 7/04*     (2006.01)
    *G06F 19/00*     (2018.01)

(56) References Cited

U.S. PATENT DOCUMENTS

2011/0092779 A1     4/2011     Chang et al.
2012/0126944 A1*     5/2012     Ueno .................. G07C 9/00158
                                                                     340/5.82
2013/0085364 A1     4/2013     Lu et al.
2014/0081087 A1*     3/2014     Yu ........................ A61B 5/6898
                                                                     600/301

FOREIGN PATENT DOCUMENTS

| CN | 101721203 A | 6/2010 |
|---|---|---|
| CN | 102450999 A | 5/2012 |
| CN | 103315712 A | 9/2013 |

OTHER PUBLICATIONS

International Search Report dated Nov. 20, 2014 corresponding to International application No. PCT/CN2014/091787.

* cited by examiner

DISPLAY SYSTEM FOR PHYSIOLOGICAL INFORMATION AND DIAGNOSTIC METHOD

This is a National Phase Application filed under 35 U.S.C. 371 as a national stage of PCT/CN2014/091787, filed Nov. 20, 2014, an application claiming the benefit of Chinese Application No. 201410145595.X, filed Apr. 11, 2014, the content of each of which is hereby incorporated by reference in its entirety.

FIELD OF THE INVENTION

The present invention relates to the field of display technology, and particularly relates to a display system and a diagnostic method.

BACKGROUND OF THE INVENTION

In today's society, with the accelerated pace of work and life, people pay more and more attention to their physical health conditions. In most cities with rapid economic development, hospitals are generally crowded, it takes time and energy to queue for registration, and as a result, treatment may even be delayed sometimes, which aggravates illness. Thus, it has become a new research and development direction in current filed of display technology how to enable a household or an individual to know physical condition thereof more conveniently and quickly in the case of physical discomfort.

In order to know a person's health condition, it is generally necessary to detect physiological information of human body, such as temperature, pulse, blood pressure, blood glucose, heart rate and the like. At present, medical detectors for detecting the physiological information of human body have been widely applied in the medical field, but the existing medical detectors inevitably have the following problems in people's daily application.

Firstly, for a large-scale medical detector, problems such as large volume, complex operation, high cost and the like always exist, which makes the large-scale medical detector not applicable to a household or an individual in general, but only applicable to medical institutions such as hospitals. Secondly, for a small-sized medical detector, since its function for detecting the physiological information is generally simple, a plurality of different medical detectors must be adopted for detection when a user needs to detect a variety of physiological information, and in this case, it is necessary to buy various small-sized medical detectors with different functions, which increases cost for diagnosis and complicates the usage.

SUMMARY OF THE INVENTION

In view of the above technical problems existing in the prior art, the present invention provides a display system and a diagnostic method. The display system can not only display an image normally, but can also obtain a diagnosis result based on the physiological information of human body, which greatly facilitates a user to diagnose the physical health status in real time, and significantly reduces the cost for diagnosing the physical health status.

The present invention provides a display system, which comprises an information preprocessing module, a display panel and a control circuit electrically connected to the display panel, the information preprocessing module is used for starting the control circuit and the display panel, the control circuit is used for controlling the display panel to display an image, and the information preprocessing module comprises a sensor used for collecting physiological information of human body;

the information preprocessing module further comprises a preprocessing circuit used for preprocessing the physiological information of human body collected by the sensor and transmitting the preprocessed physiological information of human body to the control circuit;

the control circuit is used for receiving the preprocessed physiological information of human body obtaining a diagnosis result on the preprocessed physiological information of human body; and the display panel is used for displaying the diagnosis result.

Preferably, the preprocessing circuit comprises a receiving module, an A/D conversion module, a pre-storage module and a communication module, and the receiving module, the A/D conversion module and the pre-storage module are electrically connected to the communication module, respectively, wherein the receiving module is used for receiving the physiological information of human body, in a form of analog signal, from the sensor, and transmitting the physiological information of human body in the form of analog signal to the A/D conversion module;

the A/D conversion module is used for receiving the physiological information of human body, in the form of analog signal, transmitted from the receiving module, converting the physiological information of human body from an analog signal to a digital signal, and transmitting the converted physiological information of human body in a form of digital signal to the pre-storage module;

the pre-storage module is used for receiving and storing the physiological information of human body in the form of digital signal; and the communication module is used for controlling data transmission between the information preprocessing module and the control circuit, and the transmitted data include the physiological information of human body and control instructions.

Preferably, the communication module comprises a wireless transmitting sub-module; the control circuit comprises a wireless receiving module, a storage module and a diagnosis module, which are electrically connected to each other, and the control circuit further comprises a visualization processing module, which is electrically connected to the diagnosis module and the display panel, respectively, wherein the wireless transmitting sub-module is used for transmitting the preprocessed physiological information of human body in the form of digital signal in the pre-storage module to the wireless receiving module;

the wireless receiving module is used for receiving the preprocessed physiological information of human body, in the form of digital signal, transmitted from the wireless transmitting sub-module and transmitting the physiological information of human body to the storage module and/or the diagnosis module;

the diagnosis module is used for performing internal diagnosis based on the physiological information of human body transmitted from the wireless receiving module and/or performing external diagnosis based on the physiological information of human body by means of an external cloud, so as to obtain the diagnosis result;

the storage module is used for storing the physiological information of human body transmitted from the wireless receiving module and the diagnosis result; and the visualization processing module is used for performing visualization processing on the diagnosis result and transmitting the processed diagnosis result to the display panel for display.

Preferably, the storage module further pre-stores a diagnosis database in which there is a mapping table of physiological characteristic parameters of human body and result information; and the diagnosis module comprises an extraction sub-module and a comparison sub-module, wherein:

the extraction sub-module is used for processing the physiological information of human body, extracting characteristic parameters of the physiological information of human body and transmitting the extracted characteristic parameters to the comparison sub-module;

the comparison sub-module is used for receiving the characteristic parameters extracted by the extraction sub-module, reading the mapping table in the diagnosis database pre-stored in the storage module, comparing the received characteristic parameters with the physiological characteristic parameters of human body in the mapping table, determining result information matching with the received characteristic parameters obtained through comparison as the diagnosis result, and transmitting the diagnosis result to the storage module and/or the visualization processing module.

Preferably, the control circuit further comprises a cloud transmitting module and a cloud receiving module, which are both electrically connected to the diagnosis module and the storage module, respectively, and the cloud receiving module is further electrically connected to the visualization processing module;

the cloud transmitting module is used for transmitting the physiological information of human body in the storage module to the external cloud;

the external cloud is used for obtaining the diagnosis result based on the physiological information of human body and transmitting the diagnosis result to the cloud receiving module; and the cloud receiving module is used for receiving the diagnosis result and transmitting the diagnosis result to the storage module and/or the visualization processing module.

Preferably, the communication module further comprises a switching button used for manually selecting the diagnosis module to perform internal diagnosis or selecting the external cloud to perform external diagnosis.

Preferably, the wireless transmitting sub-module comprises one of a Bluetooth transmission module, an infrared transmission module, a Wi-Fi transmission module and a ZigBee transmission module.

Preferably, the communication module is further used for controlling the receiving module, the A/D conversion module and the pre-storage module to process and transfer the physiological information of human body.

Preferably, the communication module is further used for controlling the receiving module to process and transfer the physiological information of human body, and the A/D conversion module and the pre-storage module are controlled, by means of respective enable terminals, to process and transfer the physiological information of human body.

Preferably, the display panel is capable of displaying the diagnosis result while displaying an image normally; or, the display panel only displays the diagnosis result or only displays an image normally.

Preferably, the sensor comprises at least one of a body temperature sensor, a pulse sensor, a blood pressure sensor, a blood glucose sensor and a heart sound sensor.

The present invention further provides a diagnostic method which adopts the above display system to assist in diagnosing physical health status, and comprises steps of:

collecting physiological information of human body, preprocessing the collected physiological information of human body, and then transmitting the preprocessed physiological information of human body to a control circuit;

obtaining a diagnosis result, by the control circuit, based on the preprocessed physiological information of human body, and transmitting the diagnosis result to a display panel; and displaying, by the display panel, the diagnosis result.

Preferably, the step of preprocessing the collected physiological information of human body comprises: receiving the collected physiological information of human body in a form of analog signal, converting the physiological information of human body from an analog signal to a digital signal, and pre-storing the physiological information of human body in a form of digital signal.

Preferably, the step of obtaining a diagnosis result, by the control circuit, based on the preprocessed physiological information of human body comprises: performing, by the control circuit, internal diagnosis based on the preprocessed physiological information of human body; and/or performing, by the control circuit, external diagnosis based on the preprocessed physiological information of human body by means of an external cloud, so as to obtain the diagnosis result.

Preferably, a diagnosis database is pre-stored in the control circuit, and there is a mapping table of physiological characteristic parameters of human body and result information in the diagnosis database; and the step of performing, by the control circuit, internal diagnosis based on the preprocessed physiological information of human body comprises:

processing the preprocessed physiological information of human body and extracting characteristic parameters of the physiological information of human body, by the control circuit; and comparing the extracted characteristic parameters with the physiological characteristic parameters of human body in the mapping table, and determining result information matching with the extracted characteristic parameters obtained through comparison as the diagnosis result.

Preferably, the step of performing, by the control circuit, external diagnosis based on the preprocessed physiological information of human body by means of the external cloud comprises: transmitting, by the control circuit, the preprocessed physiological information of human body to the external cloud; obtaining, by the external cloud, the diagnosis result based on the physiological information of human body, and transmitting the diagnosis result to the control circuit.

Preferably, the display panel displays the diagnosis result while displaying an image normally; or, the display panel only displays the diagnosis result or only displays an image normally.

DETAILED DESCRIPTION OF THE EMBODIMENTS

In order to enable a person skilled in the art to better understand technical solutions of the present invention, a display system and a diagnostic method according to the present invention will be further described in detail below in conjunction with the accompanying drawings and specific implementations.

Embodiment 1

Figure 1:
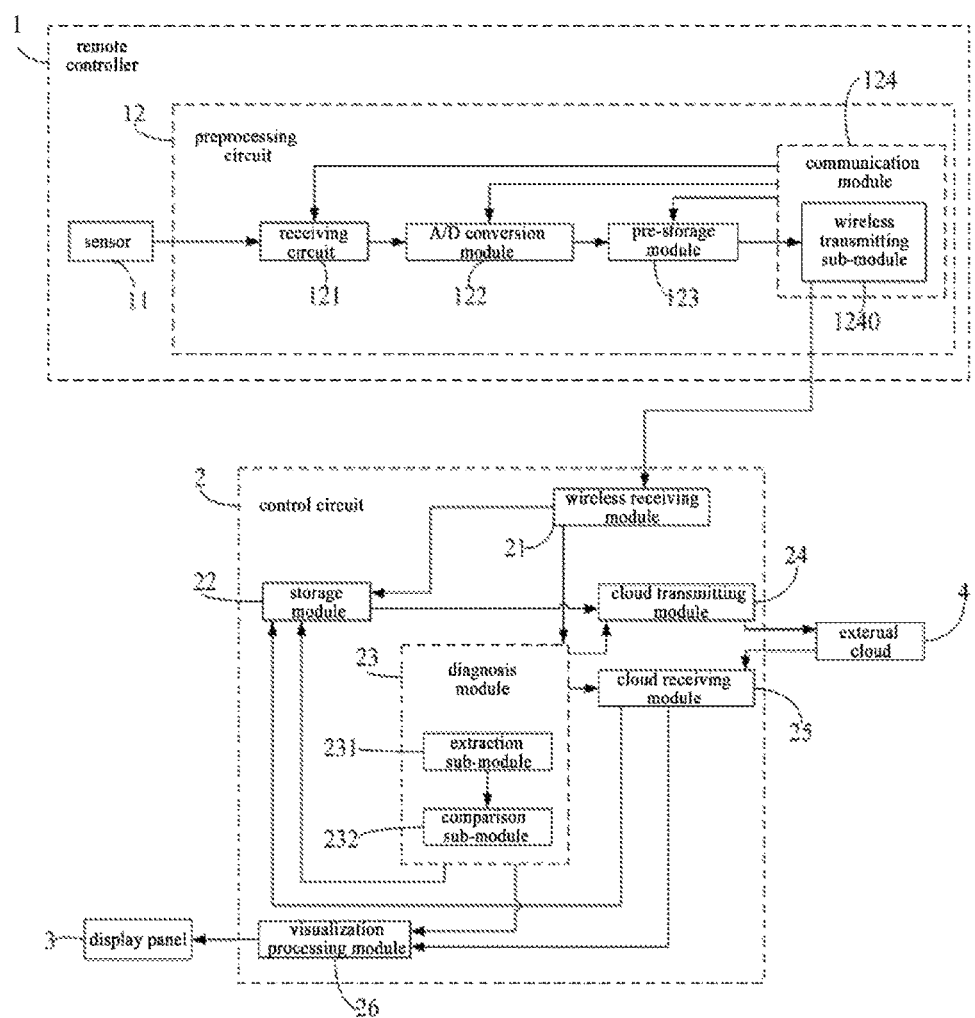
FIG. 1 is a schematic block diagram of a display system according to Embodiment 1 of the present invention.

This embodiment provides a display system which, as shown in FIG. 1, comprises an information preprocessing module 1, a display panel 3 and a control circuit 2 electrically connected to the display panel 3. Specifically, the present embodiment is described by taking a case that the information preprocessing module is a remote controller as an example. The remote controller 1 is used for starting the control circuit 2 and the display panel 3, and the control circuit 2 is used for controlling the display panel 3 to display an image. The remote controller 1 comprises a sensor 11 for collecting physiological information of human body and a preprocessing circuit 12 for preprocessing the physiological information of human body collected by the sensor 11 and sending the preprocessed physiological information of human body to the control circuit 2. The control circuit 2 is used for receiving the preprocessed physiological information of human body and diagnosing based on the physiological information of human body. The display panel 3 is used for displaying a diagnosis result.

The control circuit 2 can not only control the display panel 3 to display normally, but can also diagnose based on the preprocessed physiological information of human body, thus greatly facilitating a user to diagnose the physical health status in real time.

In the present embodiment, the preprocessing circuit 12 comprises a receiving module 121, an A/D (analog/digital) conversion module 122, a pre-storage module 123 and a communication module 124. The receiving module 121, the A/D conversion module 122 and the pre-storage module 123 are electrically connected to the communication module 124, respectively. The receiving module 121 is used for receiving the physiological information of human body, in a form of analog signal, collected by the sensor 11, and sending the physiological information of human body to the A/D conversion module 122. The A/D conversion module 122 is used for receiving the physiological information of human body, in the form of analog signal, sent from the receiving module 121, converting the physiological information of human body from an analog signal to a digital signal, and sending the converted physiological information of human body in a form of digital signal to the pre-storage module 123. The pre-storage module 123 is used for receiving and storing the physiological information of human body in the form of digital signal. The communication module 124 is used for controlling data transmission between the remote controller 1 and the control circuit 2, and the transmitted data include the physiological information of human body, control instructions and the like.

It should be noted that, in the present embodiment, the communication module 124 is further used for controlling the receiving module 121, the A/D conversion module 122 and the pre-storage module 123 to process and transfer the physiological information of human body. That is to say, the receiving module 121 receives the physiological information of human body collected by the sensor 11 only when the communication module 124 sends a receiving instruction to the receiving module 121; the A/D conversion module 122 starts to perform A/D conversion only when the communication module 124 sends a conversion instruction to the A/D conversion module 122; and the pre-storage module 123 pre-stores the physiological information of human body only when the communication module 124 sends a pre-storing instruction to the pre-storage module 123.

In the present embodiment, the communication module 124 of the remote controller 1 comprises a wireless transmitting sub-module 1240; the control circuit 2 comprises a wireless receiving module 21, a storage module 22 and a diagnosis module 23, which are electrically connected to each other, and the control circuit 2 further comprises a visualization processing module 26 which is electrically connected to the diagnosis module 23 and the display panel 3, respectively. The wireless transmitting sub-module 1240 is used for transmitting the preprocessed physiological information of human body in the form of digital signal in the pre-storage module 123 to the wireless receiving module 21; the wireless receiving module 21 is used for receiving the preprocessed physiological information of human body in the form of digital signal transmitted from the wireless transmitting sub-module 1240 and transmitting the physiological information of human body to the storage module 22 and/or the diagnosis module 23; the diagnosis module 23 is used for performing internal diagnosis based on the physiological information of human body transmitted from the wireless receiving module 21 and/or performing external diagnosis based on the physiological information of human body by means of an external cloud, so as to obtain a diagnosis result; the storage module 22 is used for storing the physiological information of human body transmitted from the wireless receiving module 21, the diagnosis result and the like; the visualization processing module 26 is used for performing visualization processing on the diagnosis result and transmitting the processed diagnosis result to the display panel 3 for display.

It should be noted that, in the present embodiment, the wireless transmitting sub-module 1240 transmits the preprocessed physiological information of human body in the form of digital signal only when the communication module 124 sends a transmitting instruction to the wireless transmitting sub-module 1240.

The storage module 22 may further pre-store a diagnosis database in which there is a mapping table of the physiological characteristic parameters of human body and result information; the diagnosis module 23 comprises an extraction sub-module 231 and a comparison sub-module 232. The extraction sub-module 231 is used for processing the physiological information of human body, extracting the characteristic parameters of the physiological information of human body and transmitting the extracted characteristic parameters to the comparison sub-module 232; the comparison sub-module 232 is used for receiving the characteristic parameters, reading the mapping table in the diagnosis database pre-stored in the storage module 22, comparing the received characteristic parameters with the physiological characteristic parameters of human body in the mapping table, determining the result information matching with the received characteristic parameters obtained through comparison as the diagnosis result, and transmitting the diagnosis result to the storage module 22. Needless to say, the comparison sub-module 232 may transmit the determined diagnosis result to the visualization processing module 26 directly, and the visualization processing module 26 performs visualization processing on the diagnosis result and then transmits the processed diagnosis result to the display panel 3 for display. For example, a heart sound signal collected by the remote controller 1 is generally weak, and mixed with noises (e.g., skin fricative, environmental noise, etc.), and thus may be processed by the extraction sub-module 231. The processing for the heart sound signal includes amplifying amplitude, filtering out noises, dividing the heart sound signal by taking a period as a unit, keeping the heart sound signal of one period, and finally obtaining the characteristic parameters (i.e., frequency, amplitude, etc.) of the heart sound signal by using time-frequency analysis algorithm. The characteristic parameters of the heart sound signal may be compared with heart sound characteristic parameters in a heart sound characteristic library by the comparison sub-module 232, so as to obtain the result information matching with the characteristic parameters of the heart sound signal, i.e., the diagnosis result for the heart sound signal; the diagnosis result for the heart sound signal is transmitted to the display panel 3 for display after processed by the visualization processing module 26.

With the diagnosis database in the storage module 22, the extraction sub-module 231 and the comparison sub-module 232, the control circuit 2 can process the physiological information of human body and diagnose, and obtain the diagnosis result, thereby greatly facilitating the user to diagnose the physical health status at home in real time. The user does not need to buy any other diagnostic devices any more, thus reducing the cost for diagnosis of physical health status.

In the present embodiment, the control circuit 2 may further comprise a cloud transmitting module 24 and a cloud receiving module 25, which are both electrically connected to the diagnosis module 23 and the storage module 22, and the cloud receiving module 25 is further electrically connected to the visualization processing module 26. The cloud transmitting module 24 is used for transmitting the physiological information of human body in the storage module 22 to an external cloud 4; the external cloud 4 is used for obtaining the diagnosis result based on the physiological information of human body and sending the diagnosis result to the cloud receiving module 25; the cloud receiving module 25 is used for receiving the diagnosis result and sending the diagnosis result to the storage module 22. Needless to say, the cloud receiving module 25 may directly send the diagnosis result to the visualization processing module 26, and the visualization processing module 26 performs visualization processing on the diagnosis result and sends the processed diagnosis result to the display panel 3 for display. The external cloud 4 is provided with professional analysis and diagnosis resources, and can diagnose more professionally and accurately based on the physiological information of human body.

With the cloud transmitting module 24 and the cloud receiving module 25, the control circuit 2 can diagnose more professionally and accurately based on the physiological information of human body by means of the external cloud 4, thus further improving diagnosis quality and enabling the user to obtain precise and comprehensive diagnosis result while staying indoors.

In the present embodiment, the communication module 124 may further comprise a switching button used for manually selecting the diagnosis module 23 to perform internal diagnosis or selecting the external cloud 4 to perform external diagnosis. The switching button may be two buttons, one of which is used for selecting the diagnosis module 23 to perform internal diagnosis, and the other of which is used for selecting the external cloud 4 to perform external diagnosis. Needless to say, the switching button may be one button, the diagnosis module 23 is selected to perform internal diagnosis when the button is pressed for once; and the external cloud 4 is selected to perform external diagnosis when the button is pressed for twice.

In the present embodiment, the wireless transmitting sub-module 1240 may include one of a Bluetooth transmission module, an infrared transmission module, a Wi-Fi transmission module and a ZigBee transmission module. These transmission modules can increase transmission efficiency of signals and thus improve diagnosis efficiency of the display system.

In the present embodiment, the display panel 3 can display the diagnosis result while displaying an image normally; alternatively, the display panel 3 only displays the diagnosis result or only displays an image normally, that is, no image is displayed when the diagnosis result is displayed, and the diagnosis result is not displayed when an image is displayed. Display of the diagnosis result on the display panel 3 enables the user to know the diagnosis result timely, thereby greatly facilitating the user to diagnose his/her physical health status in real time.

In the present embodiment, the sensor 11 may comprise at least one of a body temperature sensor, a pulse sensor, a blood pressure sensor, a blood glucose sensor and a heart sound sensor. This greatly facilitates the user to diagnose based on the physiological information of human body in real time. Preferably, the sensor 11 may comprise two or more of a body temperature sensor, a pulse sensor, a blood pressure sensor, a blood glucose sensor and a heart sound sensor, and this can facilitates the user to diagnose comprehensively based on the physiological information of human body.

Based on the above structure of the display system, the present embodiment further provides a diagnostic method which adopts the above display system to assist in diagnosing physical health status and comprises steps of: collecting physiological information of human body, preprocessing the collected physiological information of human body, and then transmitting the preprocessed physiological information of human body to a control circuit; diagnosing, by the control circuit, based on the preprocessed physiological information of human body to obtain a diagnosis result, and transmitting the diagnosis result to a display panel; and displaying, by the display panel, the diagnosis result.

The step of preprocessing the collected physiological information of human body may comprise: receiving the collected physiological information of human body in a form of analog signal, converting the physiological information of human body from an analog signal to a digital signal, and storing the physiological information of human body in a form of digital signal.

In the present embodiment, the step of diagnosing, by the control circuit, based on the preprocessed physiological information of human body to obtain a diagnosis result may comprise: performing, by the control circuit, internal diagnosis based on the physiological information of human body; and/or performing, by the control circuit, external diagnosis based on the physiological information of human body by means of an external cloud, so as to obtain the diagnosis result.

A diagnosis database may be pre-stored in the control circuit, and there is a mapping table of the physiological characteristic parameters of human body and result information in the diagnosis database. The step of performing, by the control circuit, internal diagnosis based on the physiological information of human body may comprise: processing the physiological information of human body and extracting characteristic parameters of the physiological information of human body, by the control circuit; comparing the characteristic parameters with the physiological characteristic parameters of human body in the mapping table, and determining the result information matching with the characteristic parameters obtained through comparison as the diagnosis result.

The step of performing, by the control circuit, external diagnosis based on the physiological information of human body by means of an external cloud may comprise: transmitting, by the control circuit, the physiological information of human body to the external cloud; obtaining, by the external cloud, the diagnosis result based on the physiological information of human body, and transmitting the diagnosis result to the control circuit.

In this diagnostic method, the display panel can display the diagnosis result while displaying an image normally; or, the display panel can only display the diagnosis result or only display an image normally.

Embodiment 2

Figure 2:
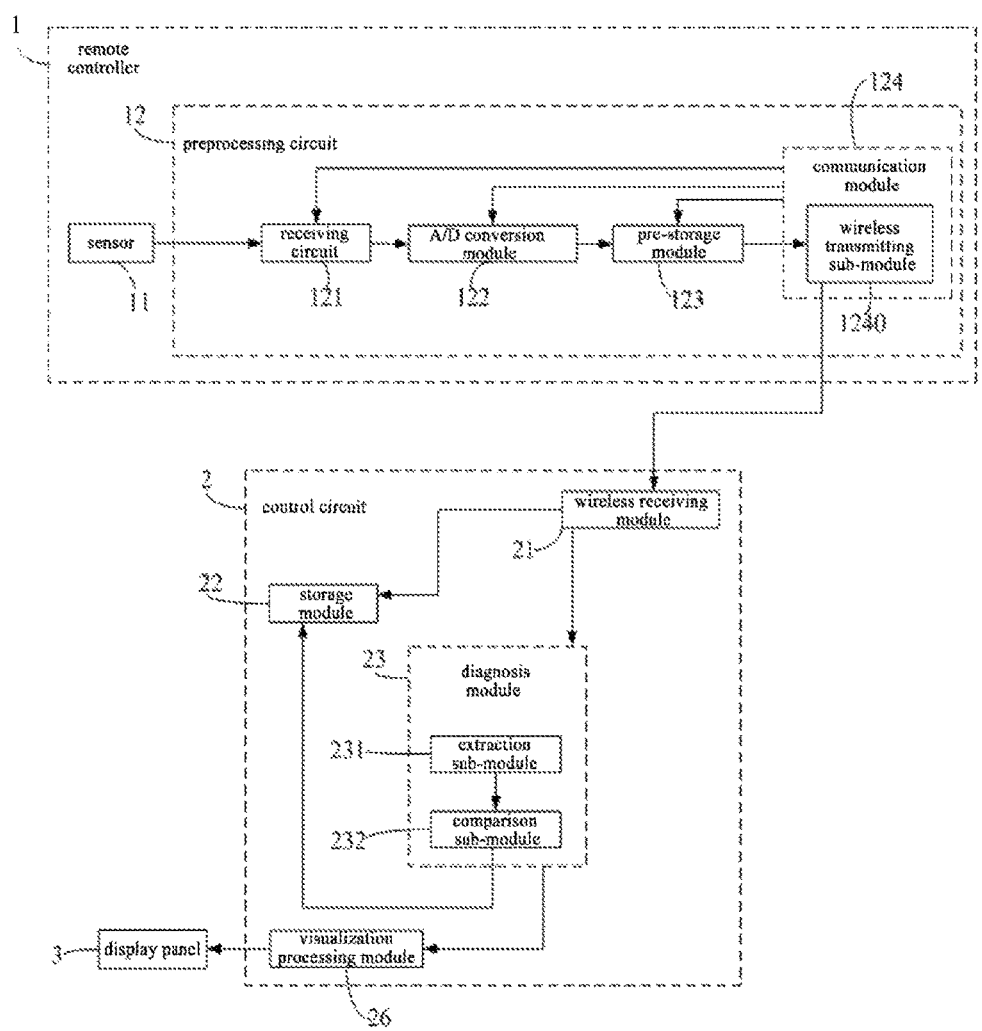
FIG. 2 is a schematic block diagram of a display system according to Embodiment 2 of the present invention.

The present embodiment provides a display system, which, as shown in FIG. 2, differs from Embodiment 1 in that the control circuit 2 in the display system only performs internal diagnosis based on the physiological information of human body by means of the diagnosis module 23. Accordingly, the control circuit 2 does not comprise the cloud transmitting module and the cloud receiving module, and the switching button may not be provided in the remote controller 1 (i.e., the information preprocessing module). Accordingly, in the present embodiment, the diagnostic method which adopts the display system to assist in diagnosing physical health status does not comprise the step of performing, by the control circuit, external diagnosis based on the physiological information of human body by means of the external cloud.

The other structures of the display system and the other steps of the diagnostic method according to the present embodiment are the same as those in Embodiment 1, and are not repeatedly described herein.

Embodiment 3

Figure 3:
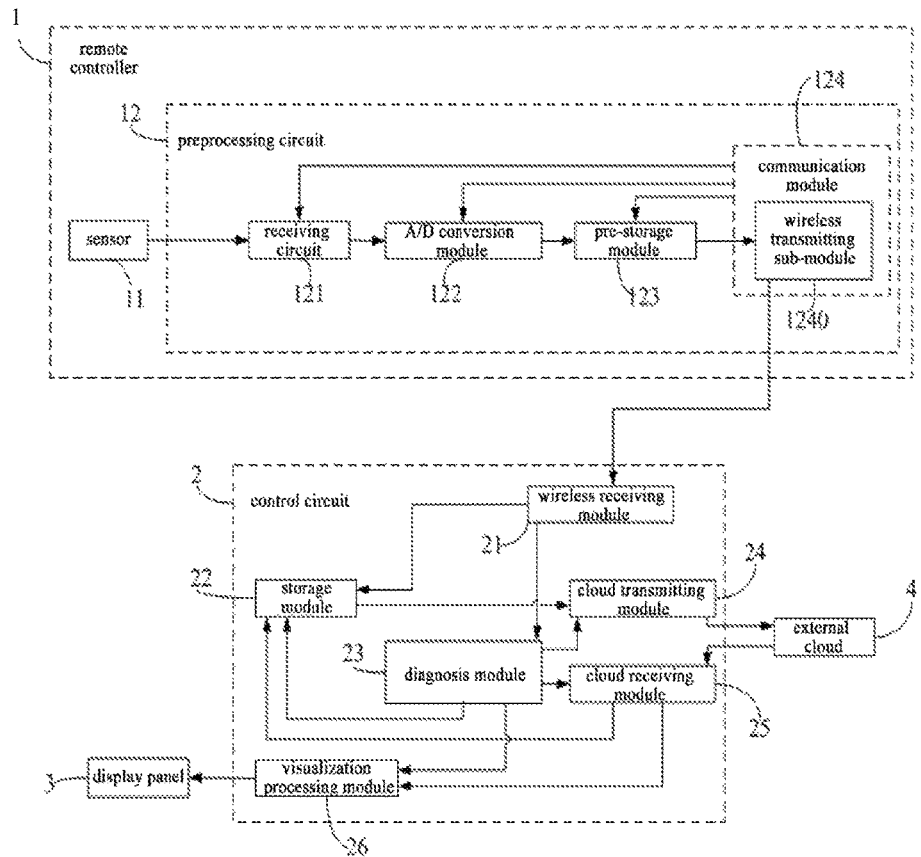
FIG. 3 is a schematic block diagram of a display system according to Embodiment 3 of the present invention.

This embodiment provides a display system, which, as shown in FIG. 3, differs from Embodiments 1 and 2 in that the control circuit 2 in the display system only performs external diagnosis based on the physiological information of human body by means of the external cloud 4. Accordingly, the diagnosis module 23 of the control circuit 2 does not comprise the extraction sub-module and the comparison sub-module; and the switching button may not be provided in the remote controller 1 (i.e., the information preprocessing module). Accordingly, in the present embodiment, the diagnostic method which adopts the display system to assist in diagnosing physical health status does not comprise the step of performing, by the control circuit, internal diagnosis based on the physiological information of human body.

The other structures of the display system and the other steps of the diagnostic method according to the present embodiment are the same as those in Embodiment 1, and are not repeatedly described herein.

Embodiment 4

Figure 4:
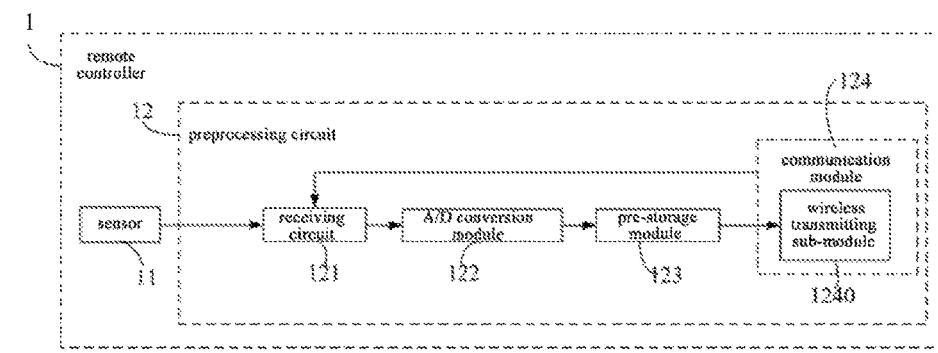
FIG. 4 is another schematic block diagram of an information preprocessing module in the display system shown in FIGS. 1 to 3.

This embodiment provides a display system, which, as shown in FIG. 4, differs from Embodiments 1 to 3 in that the A/D conversion module 122 and the pre-storage module 123 of the remote controller (i.e., the information preprocessing module) in the display system may not be controlled by the communication module 124, but controlled by means of respective enable terminals. Specifically, when the communication module 124 transmits a receiving instruction to the receiving module 121, the receiving module 121 receives the physiological information of human body collected by the sensor 11 and transmits the received physiological information of human body to the A/D conversion module 122; in response to the reception of the physiological information of human body, the enable terminal of the A/D conversion module 122 is enabled, and thus the A/D conversion module 122 automatically performs A/D conversion on the physiological information of human body and then transmits the converted physiological information of human body to the pre-storage module 123; in response to the reception of the converted physiological information of human body, the enable terminal of the pre-storage module 123 is enabled, and thus the pre-storage module 123 automatically stores the converted physiological information of human body.

The other structures of the display system and the diagnostic method according to the present embodiment are the same as those in any one of Embodiments 1 to 3, and are not repeatedly described herein.

Embodiments 1 to 4 have the following beneficial effects:

in the display system provided by Embodiments 1 to 4, the sensor in the remote controller (i.e., information preprocessing module) collects the physiological information of human body; the preprocessing circuit in the remote controller preprocesses the physiological information of human body; the control circuit diagnoses based on the preprocessed physiological information of human body to obtain the diagnosis result; and the display panel displays the diagnosis result. In this way, the display system can not only display normally, but can also diagnose based on the physiological information of human body, which greatly facilitates the user to diagnose the physical health status in real time, and significantly reduces the cost for diagnosing the physical health status.

In the diagnostic method provided in Embodiments 1 to 4, the physiological information of human body is collected and preprocessed; the control circuit diagnoses based on the preprocessed physiological information of human body to obtain the diagnosis result; and the diagnosis result is displayed. In this way, the user is greatly facilitated to diagnose the physical health status in real time, and the cost for diagnosing the physical health status is significantly reduced.

It can be understood that, the above implementations are merely exemplary implementations used for explaining the principle of the present invention, but the present invention is not limited thereto. For those skilled in the art, various modifications and improvements may be made without departing from the spirit and essence of the present invention, and these modifications and improvements are also deemed as falling within the protection scope of the present invention.

The invention claimed is:
1. A display system, comprising an information preprocessing module, a display panel and a control circuit electrically connected to the display panel, wherein the information preprocessing module is used for starting the control circuit and the display panel, wherein,
the information preprocessing module comprises a sensor used for collecting physiological information of human body;
the information preprocessing module further comprises a preprocessing circuit used for preprocessing the physiological information of human body collected by the sensor and transmitting the preprocessed physiological information of human body to the control circuit;
the control circuit is used for controlling the display panel to display an image, and further used for receiving the preprocessed physiological information of human body and diagnosing based on the physiological information of human body to obtain a diagnosis result; and
the display panel is used for displaying the diagnosis result,
wherein, the preprocessing circuit comprises a receiving module, an A/D conversion module, a pre-storage module and a communication module, the receiving module, the A/D conversion module and the pre-storage module are electrically connected to and controlled by the communication module, respectively, wherein, the receiving module is used for receiving the physiological information of human body in a form of analog signal collected by the sensor, and transmitting the physiological information of human body in the form of analog signal to the A/D conversion module; the A/D conversion module is used for receiving the physiological information of human body in the form of analog signal transmitted from the receiving module, converting the physiological information of human body from an analog signal to a digital signal, and transmitting the converted physiological information of human body in a form of digital signal to the pre-storage module; the pre-storage module is used for receiving and storing the physiological information of human body in the form of digital signal; and the communication module is used for controlling data transmission between the information preprocessing module and the control circuit, and the transmitted data include the physiological information of human body and control instructions,
wherein the communication module is further used for controlling the receiving module, the A/D conversion module and the pre-storage module to process and transfer the physiological information of human body,
the control circuit comprises a storage module and a diagnosis module, the storage module further pre-stores a diagnosis database in which there is a mapping table of physiological characteristic parameters of human body and result information, and
the diagnosis module comprises an extraction sub-module and a comparison sub-module, the extraction sub-module is used for processing the physiological information of human body, extracting characteristic parameters of the physiological information of human body, and transmitting the extracted characteristic parameters to the comparison su-module; and the comparison sub-module; and the comparison sub-module is used for receiving the characteristic parameters extracted by the extraction sub-module, reading the mapping table in the diagnosis database pre-stored in the storage module, comparing the received characteristic parameters with the physiological characteristic parameters of human body in the mapping table, determining result information matching with the received characteristic parameters obtained through comparison as the diagnosis result, and transmitting the diagnosis result to the storage module and/or the visualization processing module,
in a case that the physiological information comprises a heart sound signal, the extraction sub-module is used for amplifying amplitude, filtering out noises, dividing the heart sound signal by taking a period as a unit, keeping the heart sound signal of one period, and finally obtaining characteristic parameters of the heart sound signal by using time-frequency analysis algorithm the comparison sub-module is used for comparing the characteristic parameters of the heart sound signal with heart sound characteristic parameters in a heart sound characteristic library, so as to obtain result information matching with the characteristic parameters of the heart sound signal, as the diagnosis result for the heart sound signal.

2. The display system according to claim 1, wherein, the communication module comprises a wireless transmitting sub-module; the control circuit comprises a wireless receiving module,
and the control circuit further comprises a visualization processing module, which is electrically connected to the diagnosis module and the display panel, respectively, wherein,
the wireless transmitting sub-module is used for transmitting the preprocessed physiological information of human body in the form of digital signal in the pre-storage module to the wireless receiving module;
the wireless receiving module is used for receiving the preprocessed physiological information of human body in the form of digital signal transmitted from the wireless transmitting sub-module and transmitting the physiological information of human body to the storage module and/or the diagnosis module;
the diagnosis module is used for performing internal diagnosis based on the physiological information of human body transmitted from the wireless receiving module and/or performing external diagnosis based on the physiological information of human body by means of an external cloud, so as to obtain the diagnosis result;
the storage module is used for storing the physiological information of human body transmitted from the wireless receiving module and the diagnosis result; and
the visualization processing module is used for performing visualization processing on the diagnosis result and transmitting the processed diagnosis result to the display panel for display.

3. The display system according to claim 2, wherein, the control circuit further comprises a cloud transmitting module and a cloud receiving module, which are both electrically connected to the diagnosis module and the storage module, respectively, the cloud receiving module is further electrically connected to the visualization processing module;
the cloud transmitting module is used for transmitting the physiological information of human body in the storage module to the external cloud;
the external cloud is used for obtaining the diagnosis result based on the physiological information of human body and transmitting the diagnosis result to the cloud receiving module; and the cloud receiving module is used for receiving the diagnosis result and transmitting the diagnosis result to the storage module and/or the visualization processing module.

4. The display system according to claim 2, wherein, the communication module further comprises a switching button used for manually selecting the diagnosis module to perform internal diagnosis or selecting the external cloud to perform external diagnosis.

5. The display system according to claim 2, wherein, the wireless transmitting sub-module comprises one of a Bluetooth transmission module, an infrared transmission module, a Wi-Fi transmission module and a ZigBee transmission module.

6. The display system according to claim 1, wherein, the display panel is capable of displaying the diagnosis result while displaying an image normally; or, the display panel only displays the diagnosis result or only displays an image normally.

7. The display system according to claim 1, wherein, the information preprocessing module may be a remote controller.

8. The display system according to claim 1, wherein, the sensor comprises at least one of a body temperature sensor, a pulse sensor, a blood pressure sensor, a blood glucose sensor and a heart sound sensor.

9. A diagnostic method, which adopts the display system according to claim 1 to assist in diagnosing physical health status, and comprises steps of:
  collecting physiological information of human body, preprocessing the collected physiological information of human body, and then transmitting the preprocessed physiological information of human body to a control circuit;
  diagnosing, by the control circuit, based on the preprocessed physiological information of human body to obtain a diagnosis result, and transmitting the diagnosis result to a display panel; and
  displaying, by the display panel, the diagnosis result;
  wherein the step of preprocessing the collected physiological information of human body comprises: receiving, by the receiving module, the collected physiological information of human body in a form of analog signal, converting, by the A/D conversion module, the physiological information of human body from an analog signal to a digital signal, and storing, by the pre-storage module, the physiological information of human body in a form of digital signal; and
  the receiving module receives the physiological information of human body upon receipt of a receiving instruction from the communication module; the A/D conversion module starts to perform A/D conversion upon receipt of a conversion instruction from the communication module; and the pre-storage module pre-stores the physiological information of human body upon receipt of a pre-storing instruction from the communication module.

10. The diagnostic method according to claim 9, wherein, the step of diagnosing, by the control circuit, based on the preprocessed physiological information of human body to obtain a diagnosis result comprises: performing, by the control circuit, internal diagnosis based on the preprocessed physiological information of human body; and/or performing, by the control circuit, external diagnosis based on the preprocessed physiological information of human body by means of an external cloud, so as to obtain the diagnosis result.

11. The diagnostic method according to claim 10, wherein, a diagnosis database is pre-stored in the control circuit, and there is a mapping table of physiological characteristic parameters of human body and result information in the diagnosis database; and the step of performing, by the control circuit, internal diagnosis based on the preprocessed physiological information of human body comprises:
  processing the preprocessed physiological information of human body and extracting characteristic parameters of the physiological information of human body, by the control circuit; and
  comparing the extracted characteristic parameters with the physiological characteristic parameters of human body in the mapping table, and determining result information matching with the extracted characteristic parameters obtained through comparison as the diagnosis result.

12. The diagnostic method according to claim 10, wherein, the step of performing, by the control circuit, external diagnosis based on the preprocessed physiological information of human body by means of the external cloud comprises: transmitting, by the control circuit, the preprocessed physiological information of human body to the external cloud; obtaining, by the external cloud, the diagnosis result based on the physiological information of human body, and transmitting the diagnosis result to the control circuit.

13. The diagnostic method according to claim 10, wherein, the display panel displays the diagnosis result while displaying an image normally; or, the display panel only displays the diagnosis result or only displays an image normally.

14. The diagnostic method according to claim 9, wherein, the display panel displays the diagnosis result while displaying an image normally; or, the display panel only displays the diagnosis result or only displays an image normally.

* * * * *